United States Patent

Ganguly et al.

[11] Patent Number: 5,964,710
[45] Date of Patent: Oct. 12, 1999

[54] SYSTEM FOR ESTIMATING BLADDER VOLUME

[75] Inventors: Dipankar Ganguly, San Jose, Calif.;
Thomas L. Roberts, Snohomish;
Robert F. McConaghy, Kirkland, both of Wash.

[73] Assignee: SRS Medical, Inc., Burlington, Mass.

[21] Appl. No.: 09/044,525

[22] Filed: Mar. 13, 1998

[51] Int. Cl.⁶ ........................................................ A61B 8/00
[52] U.S. Cl. .............................................................. 600/449
[58] Field of Search ..................................... 600/437, 440, 600/443, 447–451, 454–455; 128/916

[56] References Cited

U.S. PATENT DOCUMENTS

| | | |
|---|---|---|
| 4,341,120 | 7/1982 | Anderson . |
| 4,852,578 | 8/1989 | Companion et al. . |
| 4,926,871 | 5/1990 | Ganguly et al. . |
| 5,058,591 | 10/1991 | Companion et al. . |
| 5,195,521 | 3/1993 | Melton, Jr. et al. ................. 600/441 X |
| 5,235,985 | 8/1993 | McMorrow et al. . |

*Primary Examiner*—Francis J. Jaworski
*Attorney, Agent, or Firm*—Cesari and McKenna, LLP

[57] ABSTRACT

A system for estimating the volume of fluid in the bladder sequentially scans the bladder with ultrasonic beams that section the bladder into a number of transverse planes. The system determines, from the scan lines associated with a given plane, a plurality of points on each of the front and back walls of the bladder. It then fits a curve to the set of front wall points and another curve to the set of back wall points, to determine an outline of the bladder in the plane. The system next calculates the cross sectional area of the bladder in the plane based on the two curves. After determining the area in each of the planes, the system determines the volume of the bladder by summing weighted version of the planar areas. The system includes a transducer that consists of a plurality of piezo-electric elements held in a relatively thin elastomeric pad and/or substrate that is acoustically impedance matched to skin. The elements are spaced and grouped such that the acoustic beams they produce lie on the plurality of planes, with the first and the last planes separated by approximately seventy degrees. The estimated volume may be is compared with a predetermined overflow threshold, to determine if the user should then void. The system may include a timer that controls the times at which the system produces estimates. The time may decrease the time between estimate calculations if the estimated volume exceeds a predetermined percentage of the overflow threshold.

22 Claims, 6 Drawing Sheets

SYSTEM FOR ESTIMATING BLADDER VOLUME

FIELD OF INVENTION

This invention relates to systems for non-invasively monitoring the volume of urine in the bladder.

BACKGROUND OF THE INVENTION

Information about the volume of urine in the bladder is important clinically for several types of patients suffering from bladder dysfunctions. For patients with neurogenic bladders, in whom the nervous system connections between the brain and the urinary bladder have been severed due to spinal cord injury or other disease conditions, sensations that normally alert individuals to the need for voiding a substantially filled bladder are either significantly reduced or absent altogether. Such patients are thus at risk of bladder overdistention, which is a condition that, if left untreated, can lead to permanent kidney damage and subsequent renal failure.

For patients with benign prostatic hyperplasia, which results in an enlarged or congested prostate, urine may be retained in the bladder after voiding. In a substantial percentage of such cases, the prostate growth constricts the urethra and thus restricts the flow of urine from the bladder. In response, the bladder grows thicker and stronger, to compensate for the increased resistance. Eventually, however, the bladder is no longer able to fully overcome the resistance and emptying becomes incomplete.

The retention of urine in the bladder puts the patient at risk of infection and bladder overdistention. Bacteria present in the urinary tract tend to multiply in the retained urine, and urinary infection can occur. The infection, in turn, can worsen the swelling already present in the prostate, and in the long run can lead to bladder stones or permanent kidney damage. The amount by which the prostate is enlarged correlates poorly with the degree of obstruction that the prostate presents to the flow of urine through the urethra. It is therefore important that patients with benign prostatic hyperplasia be monitored to determine the amount of retained urine after every voiding attempt.

Information about the volume of urine in the bladder is important also for individuals afflicted with urinary incontinence, especially overflow incontinence. Urinary incontinence is characterized by an involuntary loss of urine of sufficient quantity and/or frequency to become a social and health problem. There are two broad classes of incontinence, namely, transient and established. Transient incontinence, which is commonly caused by an acute illness or the administration of certain therapeutic drugs, is generally cured by treating the condition that caused the incontinence.

Established incontinence, on the other hand, is chronic and is generally caused by abnormalities in the function of the detrusor, the bladder outlet, or both. In many of these patients, the probability of a voiding accident increases sharply when the volume of urine in the bladder crosses an overflow threshold. While this threshold may vary from patient to patient, it is a widely held clinical belief that there exists a minimum overflow threshold that can be used as an effective predictor of such an accident in essentially every patient. Consequently, knowledge that the urine volume has crossed such a minimum threshold is useful in preventing leakage accidents.

Another class of patients for whom bladder volume information is important is patients undergoing lengthy surgery. In such patients, overdistention may occur as a result of anesthesia induced paralysis. Currently, these patients routinely have their bladders intubated with in-dwelling Foley catheters. The catheters are used to assess urine output and thereby monitor renal function and prevent bladder over distention. In-dwelling catheters, however, are major sources of infection. Furthermore, their use in urine output monitoring is labor intensive and cumbersome. Hence the use of a non-invasive and automatic process for this function is desirable.

Ultrasonic systems that use information contained in the backscattered echoes from the bladder region to determine its volume are known. One such system uses a specialized two-dimensional array transducer whose individual elements are activated simultaneously in two groups to produce first a composite transmit beam and then a composite receive beam. The signal associated with this composite receive beam is processed to extract three dimensional information about the bladder, which in turn is used to calculate its volume. To produce these two composite beams, the transducer has to be operated as a phased array; making it complex to manufacture, expensive and too bulky to be worn continuously.

Another known system uses an ultrasonic transducer that produces a single beam of ultrasonic energy. The signal received by the transducer contains information about the energy reflected from the back wall of the bladder, and the system uses an empirically developed calibration curve to indirectly relate this information to the degree of bladder distention. Consequently, the system produces only relative estimates of the bladder distention, rather than estimates of the bladder volume.

Yet another known system produces ultrasound measurements along two orthogonal planes that are each essentially normal to the direction of the patient's spine. Based on the measurements and an ellipsoidal model of the bladder, the system determines an estimate of bladder volume. The apparatus requires an operator to position and manipulate the associated transducer in a particular way in order to obtain the ultrasonic measurements, and thus, the system determines the bladder volume on an event-by-event basis. Accordingly, this system is not capable of automatically and/or essentially continuously producing the measurements necessary to produce estimates of bladder volume.

SUMMARY OF THE INVENTION

The invention is a monitoring system that sequentially scans a bladder with ultrasonic beams that section the bladder into a plurality of transverse planes. The system determines, from the scan lines associated with a given plane, a plurality of points on each of the front and back walls of the bladder. It then fits a curve to the set of front wall points and another curve to the set of back wall points, to determine an outline of the bladder in the plane. The system next calculates the cross sectional area of the bladder in the plane based on the two curves. After determining the area in each of the planes, the system determines the volume of the bladder essentially by summing weighted versions of the planar areas.

The system includes a transducer that consists of a plurality of piezo-electric elements held in a relatively thin elastomeric pad and/or substrate that is applied to the user's lower abdomen. The elements are spaced and grouped such that the acoustic beams they produce lie on the plurality of planes, with the first and the last planes separated by approximately seventy degrees.

The spacing and grouping of the piezo-electric elements is fixed, and thus, the planar areas can be combined, after each is multiplied by an appropriate design constant that is based on the angles of separation of the planes. The estimated volume may be compared with a predetermined threshold, to determine if the user should then void.

The transverse planes have been selected such that the associated measurements cover the portion of the bladder that expands in response to the volume of urine retained in the bladder. While the bladder may also expand outside of the region covered by the planes, such expansion is generally not large enough relative to the expansion within the measured region to render the volume estimate inaccurate for the purpose of determining clinically relevant bladder volumes.

The transducer elements are sized to provide divergent beams, when they are operated at their resonant frequency. Accordingly, the precise positioning of the elements on the body is not critical, and the transducer need not be repositioned for each monitoring procedure. The elastomer that houses the elements is impedance matched with the skin, and thus, ultrasound gel or a gel substitute is not required. At the interface with the skin the beams refract, such that the beams can be launched at angles greater than the tilt of the respective individual elements. The substrate in which the elements are mounted can thus be made relatively thin, so that the transducer can be continuously worn by the user. This is in contrast to prior known systems, which use transducers that are too bulky to be worn comfortably and unobtrusively by most users.

The system may automatically monitor the volume of urine in the bladder over time under the control of a timer. Further, the system may retain volume estimates calculated over predetermined periods of time, to provide patient histories from which, for example, incontinence patterns can be developed.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
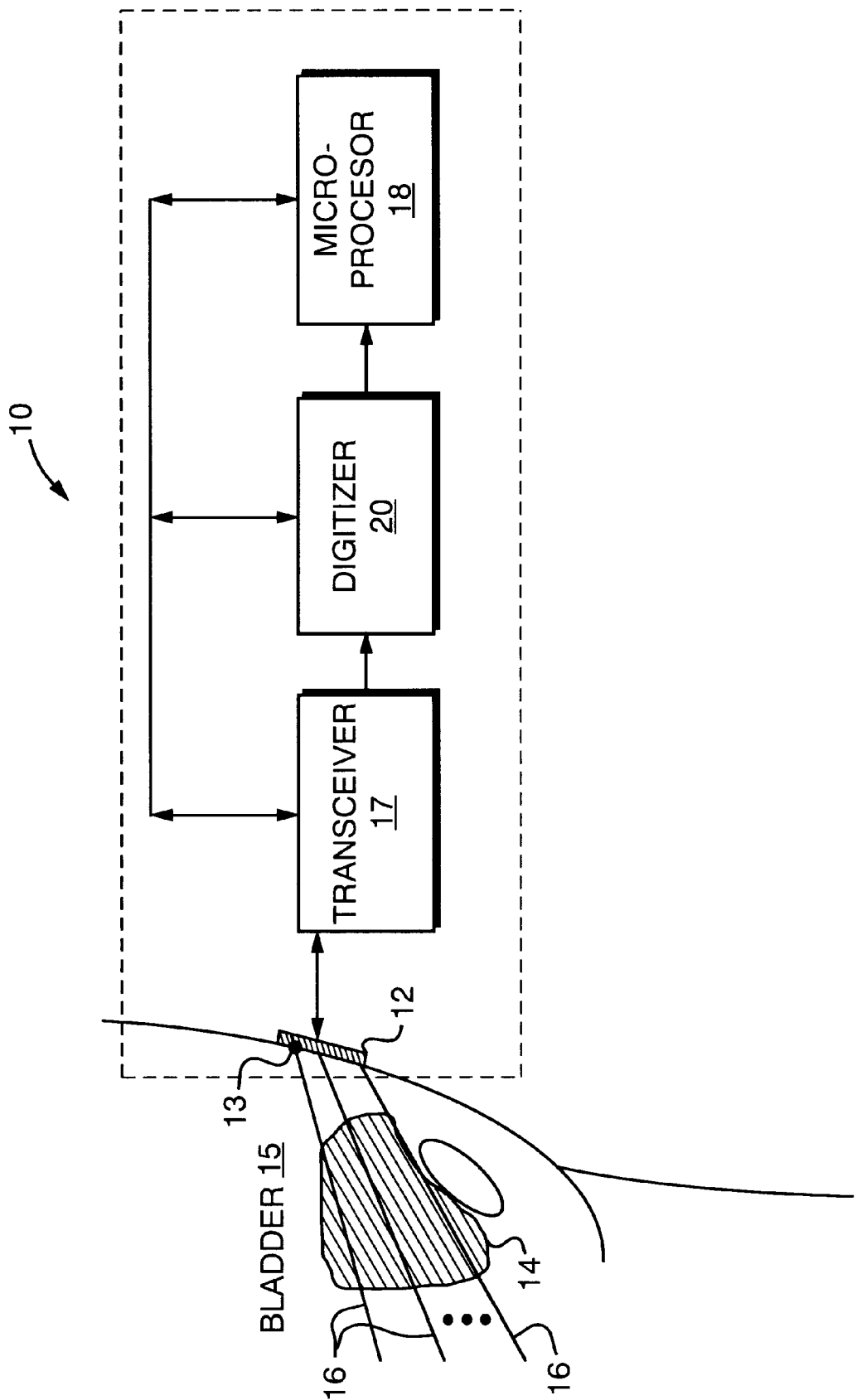
FIG. 1 is a functional block diagram of a system constructed in accordance with the invention.

Referring to FIG. 1, a monitoring system 10 for estimating the volume of urine in the bladder includes a transducer 12 that transmits ultrasonic beams into the bladder region of a patient 15. The transducer, which is discussed in more detail below with reference to FIG. 5, includes a plurality of piezo-electric elements 13 that are grouped and spaced to produce beams that span each of a plurality of transverse planes 16, which lie within a predetermined region of the bladder 14. The transducer 12 produces at least "NP" beams, with at least N beams spanning each of P transverse planes.

The transducer 12 also receives echoes of the tissue structure encountered by the beams, or what are commonly referred to as "A-lines," and supplies corresponding signals to a transceiver 18. The transceiver 18 amplifies and demodulates these signals in a conventional manner and supplies them to a digitizer 20, which produces corresponding digital signals also in a conventional manner. The digitizer 20 then provides the digital signals to a processor 18 which, as discussed below with reference to FIGS. 2–4, calculates an estimate of the volume of urine contained in the bladder based on the locations of the bladder walls in each of the planes.

Figure 2:
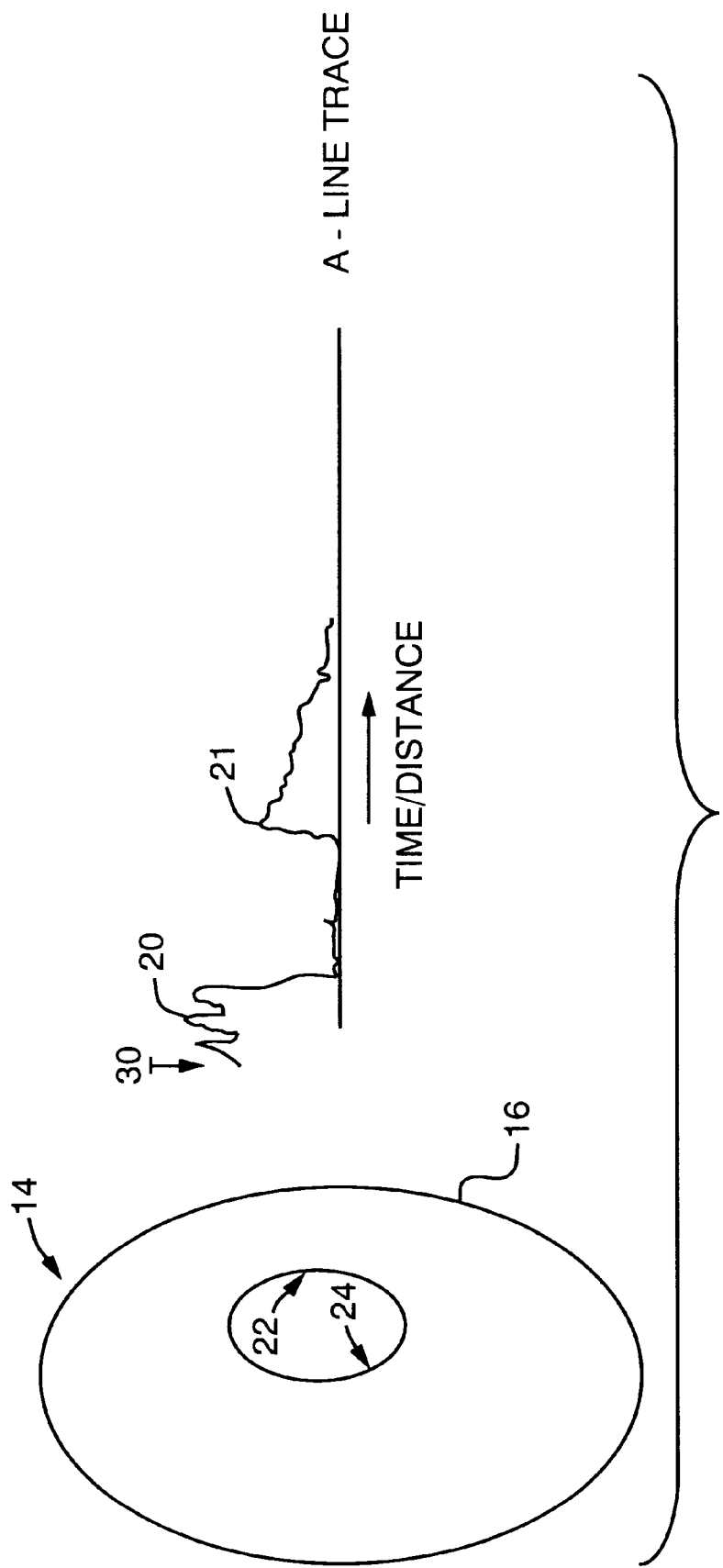
FIG. 2 is a schematic representation of a bladder signature in an A-line.

The ultrasonic beams produced by the transducer 12 are partially reflected by the skin, the front wall of the bladder and the back wall of the bladder, each of which is at a different distance from the transducer. The beams pass with little or no reflection through the fluid contained in the bladder. The bladder thus produces a recognizable pattern, or signature, in the A-line, since the bladder is the only fluid-filled region in that part of the body. The pattern that corresponds to the bladder is depicted in FIG. 2. The A-line signals produced by the transducer 12 are "noisy," however, and the changes in amplitude that represent the bladder walls difficult to discern. The system thus processes these signals to remove the noise.

Referring now also to FIG. 2, the processor 18 determines the locations of the front and back walls 22 and 24 of the bladder in each plane 16 based on the associated A-line signals 30, which are now in digital form. As discussed below, the processor filters each A-line signal, to remove the noise and enhance rising and falling edges that signify the bladder walls. The processor then determines the location of the front and back walls in each A-line, by locating the appropriate edges, which are now peaks in the filtered digital signal.

The processor thus determines N points 20 on the front wall 22 and N points 21 on back wall 24 in each plane. The processor 18 next determines a first curve 28 that best fits the N points 20 on the front wall and a second curve 30 that best fits the N points 21 on the back wall. The two curves define a cross section of the bladder in the plane, and the processor next calculates the cross-sectional area of the bladder in the plane.

After determining the cross-sectional areas in the P planes, the processor 18 calculates an estimate of the volume of urine in the bladder, by weighting and combining the P areas. The processor may then compare the estimated volume with a predetermined minimum threshold for voiding, and set off an alarm if the volume meets or exceeds the threshold. The operations of the processor 18 are discussed in even more detail with reference to FIGS. 3-4 and 6 below.

Figure 3:
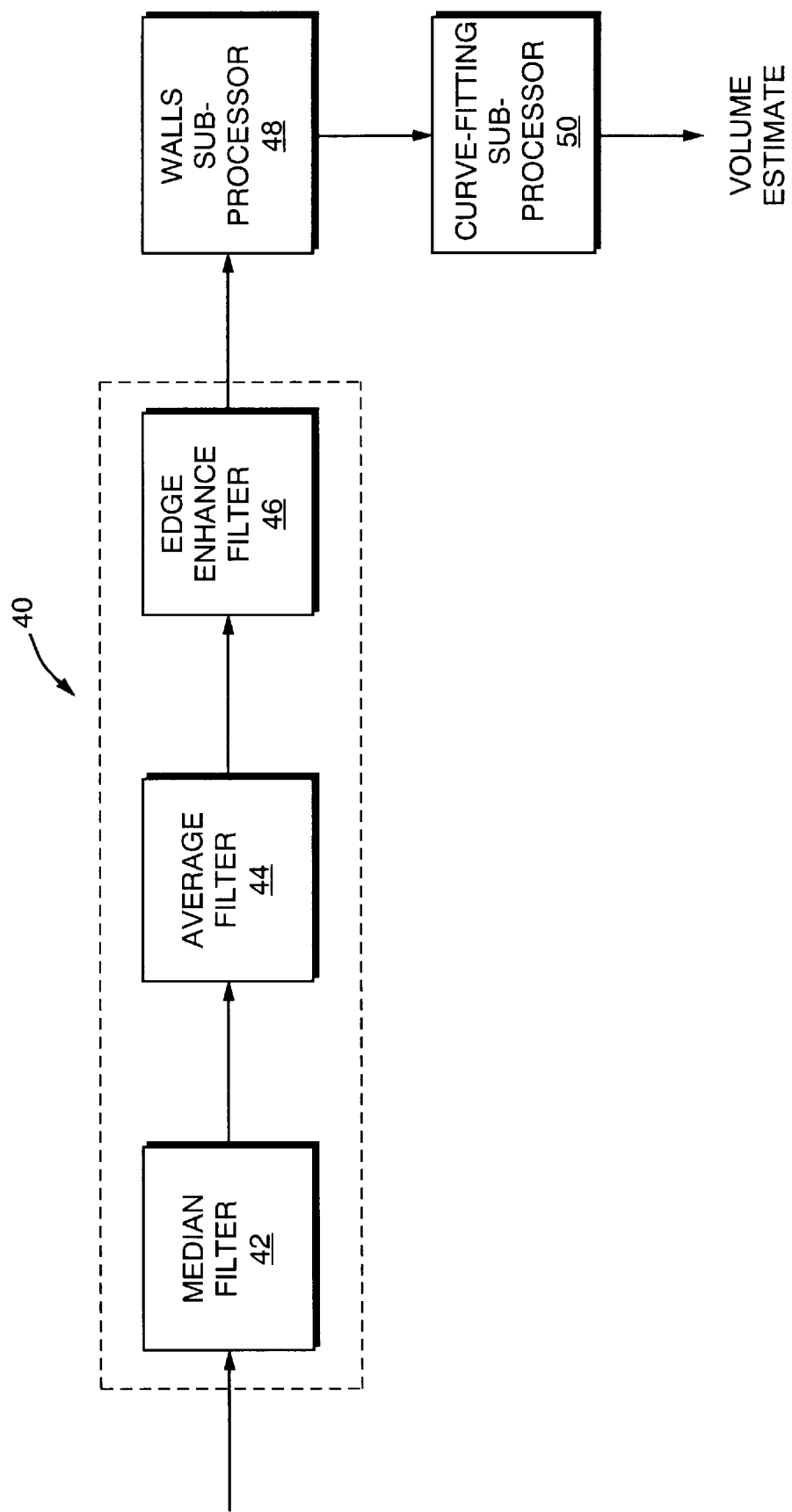
FIG. 3 is a functional block diagram of a processor in the system of FIG. 1.

Referring now to FIG. 3, the processor 18 receives the digital A-line signal and filters the signal in a filter 40 that includes one or more of a median filter 42, an averaging filter 44 and an edge enhancing filter 46. We discuss below a system that includes all three filters.

The A-line signal is first supplied to the median filter 42, which operates in a conventional manner to remove noise spikes from the signal and reduce somewhat the various other excursions in the signal that are attributable to the noise. In the system of FIG. 3, the median filter 42 is a five-point filter. The filter operates by sliding a five-point window across the digitized data associated with a given A-line. If, for example, an A-line is represented by "M" digitized points, the filter positions the five-point window over the first five data points and selects the median of the five data points within the window as the median filter output value for the $i^{th}$ data point, where i=3 in the example. The system then replaces the i=3 data point with the median filter output value. The filter next slides the window over by one data point, to determine a median filter output value for the i=4 data point. The filter repeats this process for the $i^{th}$ data points, where i=5, 6 . . ., M−3.

The width of the filter window may be set to a larger or smaller value. Alternatively, the width of the filter window may be set adaptively as a small percentage of the distance between the front and back walls of the bladder calculated from previous A-line data. The calculation of the distance "d" between the bladder walls is discussed below.

The output values produced by the median filter 42 are supplied to an averaging filter 44. The averaging filter operates in a conventional manner to smooth the data and further reduce the adverse effects of noise in the signal. In the system of FIG. 3, the averaging filter 44 is an eleven-point filter. The averaging filter thus slides an eleven-point window across the data and replaces the digital value of the $i^{th}$ point with the average value of the $i-5^{th}$ through $i+5^{th}$ points for i=6, 7 . . . M−5. By including the median filter before the averaging filter, spike noise is eliminated. This, in turn, reduces the biasing that would otherwise be introduced by the averaging filter. A smaller or greater number of points may be used in the averaging filter window. Alternatively, the width of the filter window may be set adaptively as a small percentage of the distance, d, between the front and back walls of the bladder calculated from previous A-line data.

The output values produced by the averaging filter 44 are supplied to the edge enhancing filter 46, which manipulates the signal in a conventional manner in accordance with a derivative-based operator. In the system of FIG. 3, the edge enhancing filter consists of a three-point kernel [0, 6,−1] that slides across the data. For the $i^{th}$ data point, the filter produces a filter output value that is the sum of the $i-1^{st}$, and $i^{th}$ and $i+1^{st}$ data points multiplied by the respective elements of the kernal. Specifically, the sum of the $i-1^{st}$ data point multiplied by 0, the $i^{th}$ data point multiplied by 6 and the $i+1^{st}$ data point multiplied by −1. The filter replaces the i=2, 3, . . . M−2 data points with the corresponding filter output values. A greater or smaller number of points may be used in the edge enhancing filter, with corresponding changes made to the kernal.

The filtered signal is next supplied to a wall sub-processor 48, which determines the locations of the front and back walls of the bladder by determining, respectively, the locations of associated peaks in the filtered, digital signal. The portion of the signal that corresponds to the first 2.5 cm of the body includes reflections from the skin that generally saturate the receiver, and the wall sub-processor 48 thus ignores that portion of the signal. Each digital signal value, or sample, is associated with a location index that is converted to centimeters by multiplying the index by a conversion constant "v," which is based on the velocity of sound. Accordingly, the wall sub-processor ignores the first 50 digital values.

The sub-processor determines the location "$L_F$" of the front wall by finding the location of an appropriate peak in the remaining signal. To do this, the sub-processor 48 calculates the difference between the first two digital values in the remaining signal and compares the difference value with a predetermined threshold. If the difference exceeds the threshold, the processor selects for the front wall the location of the first of the two associated digital values, that is, the point that is closer to the transducer. If the difference does not exceed the threshold, the sub-processor calculates the difference between the digital values associated with the second of the signal samples used in the previous difference calculation and the digital value associated with the next signal sample, compares the difference to the threshold, and so forth, until the front wall is located.

Once the front wall is located, the sub-processor searches for the back wall. To determine the location "$L_B$" of the back wall in the A-line signal, the sub-processor searches the remaining signal for any peak that exceeds a predetermined second threshold. The sub-processor thus calculates the difference between each set of two adjacent digital values and compares the difference values with the second threshold. If more than one peak is found, the system determines if the difference value associated with one of the peaks is at least 3 times greater than each of the difference values associated with the other detected peaks. If so, the sub-processor selects as the back wall location the point that corresponds to the first of the two digital values associated with the greatest difference. If only two peaks are found and the associated difference values differ by less than a factor of 3, the sub-processor selects the peak that is farther from the transducer. If three or more peaks are found and associated difference values differ by less than a factor of three, the wall sub-processor identifies a "cluster," which is a set two or more peaks that are located within 10 signal samples of each other. The sub-processor then selects as the location of the back wall the position of the median peak within the cluster.

The wall sub-processor also determines the distance "d" in centimeters between the front and back walls as: $d=(L_B-L_F) * v$, where "*" represents multiplication. The sub-processor 46 supplies the location indices $L_F$ and $L_B$ and the corresponding distance d to a curve-fitting sub-processor 50. The curve fitting sub-processor holds the values until each A-line associated with a given plane has been processed.

The sub-processor 50 determines if the location of the back wall is within a 4.5 cm "dead zone" following the front wall location. The dead zone corresponds to a bladder that contains less than 40 ccs of urine, which is less than a clinically relevant, minimum volume. If the back wall location falls within the dead zone in each A-line associated with the plane, the sub-processor does not calculate an area measurement. If the back wall location falls within the dead zone in all of the planes, the sub-processor does not calculate the area in any plane, and thus, the system does not calculate a volume is estimate at this time.

In the event that the sub-processor 50 determines that only a relatively small number of backwall points fall outside of the dead zone, and that there are thus not enough points to compute the volume, sub-processor 50 instructs the system to produce another set of A-lines and attempt to locate the back wall in these A-lines. The system repeats the process a total of three times, as necessary. If, after three attempts, the system still does not have a sufficient number of back wall points, the system sounds or excites an alarm that indicates that the transducer requires repositioning.

Once all of the A-lines have been processed for a particular plane, the curve-fitting sub-processor 50 determines the cross-sectional outline of the bladder in the plane. The processor determines a first curve that best fits the set of N front wall points and a second curve that best fits the set of N back wall points.

Figure 4:
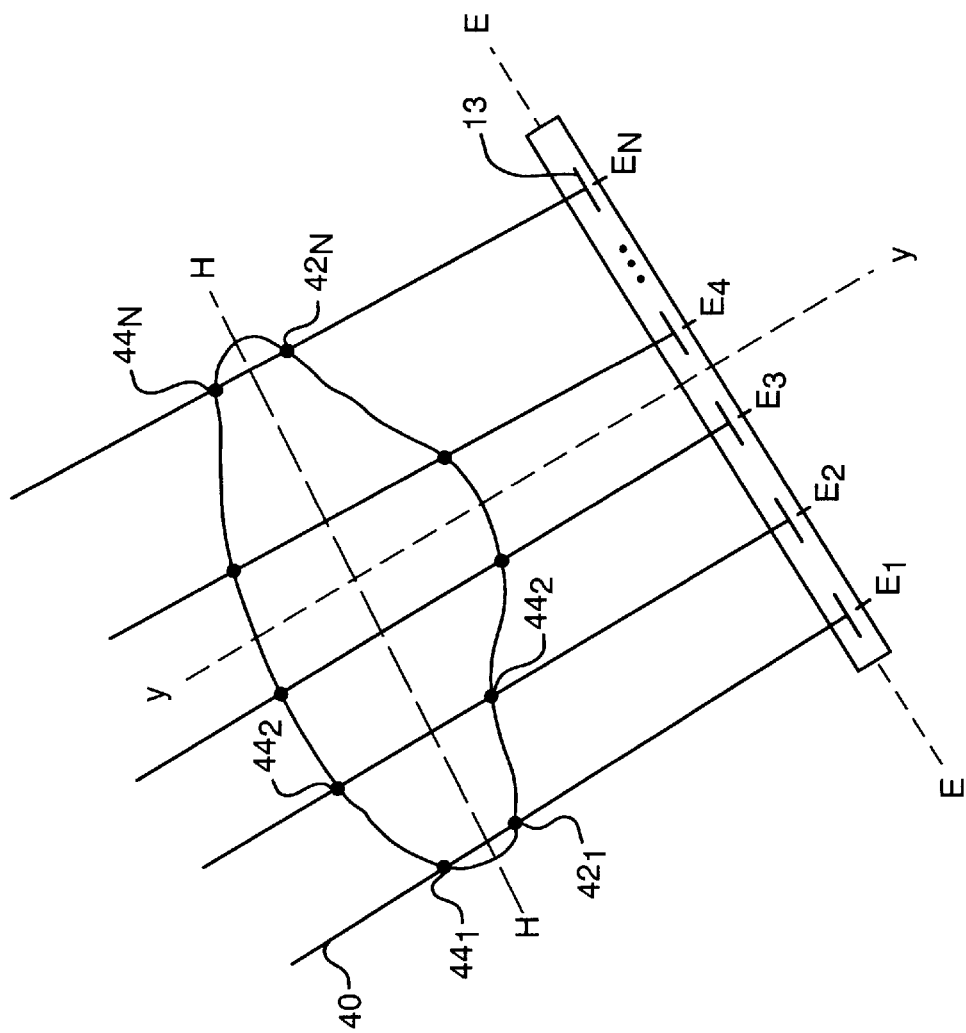
FIG. 4 is a diagram of a section of a bladder partitioned into a plane by a set of acoustic beams.

Referring now also to FIG. 4, the sub-processor 50 determines x and y coordinates of the front and back wall points relative to an X axis that is a line E—E, which extends through the piezo-electric elements $E_1 \ldots E_N$, and a Y axis, which is a line Y—Y that is perpendicular to the line E—E and extends through the mid-point of the line E—E. The sub-processor determines a mid-point between the front wall and back wall locations 42 and 44 in a first A-line 40 that corresponds to the first piezo-electric element $E_1$ associated with the plane. It then determines the equation of a line H—H that intersects the A-line 40 at the mid point and is parallel to the line E—E.

The sub-processor 50 next determines the equation $S_B$ of a curve through the back wall points that are above line H—H, by determining the coefficients of a degree "q" polynomial, $S_B \equiv Y = \Sigma a_j x^j$ for j=0, 1 . . . q where in this system q=N−1, and N is the number of A-lines that span the plane. Following the method of least squares, the system solves the following set of normal equations to determine the coefficients $a_j$: for i=1, 2 . . . N−1

$$\sum_{j=1}^{q} \left( \sum_{k=1}^{N} x_k^{j+i} \right) a_j = \sum_{k=1}^{N} x_k^i y_k$$

where $x_k$ and $y_k$ are the x and y coordinates of the known points on the back wall.

The system similarly determines the equation $S_F$ of a curve through the known points on the front wall that are below the line H—H. It next determines the points U and V where the curves $S_F$ and $S_B$ intercept the line H—H. These points are the bounds of integration to determine the area $A_B$ below the curve $S_B$, and the area $A_F$ below the curve $S_F$. The area bounded or enclosed by the curves $S_F$ and $S_B$, which is $A_B - A_L$, is the cross-sectional area of the bladder in the plane.

To determine the area $A_B$ below the curve $S_B$, the system uses Simpson's Rule for degree q polynomials and numerically solves the equation:

$$\int_v^u S_B \, dx = A_B$$

The sub-processor similarly determines the area $A_F$ below the curve $S_F$, and then subtracts the two areas to produce the estimated area of the bladder in the plane.

The sub-processor then calculates the cross-sectional area in each of the remaining P planes.

Once the areas in all P planes are calculated, the sub-processor sums them, after weighting each one by an associated design constant $D_P$, for p=1, 2 . . . . P. The design constant is associated with the angle between the $p^{th}$ plane and a first, essentially horizontal, plane. The sum is an estimate of the volume in the bladder.

Figure 5:
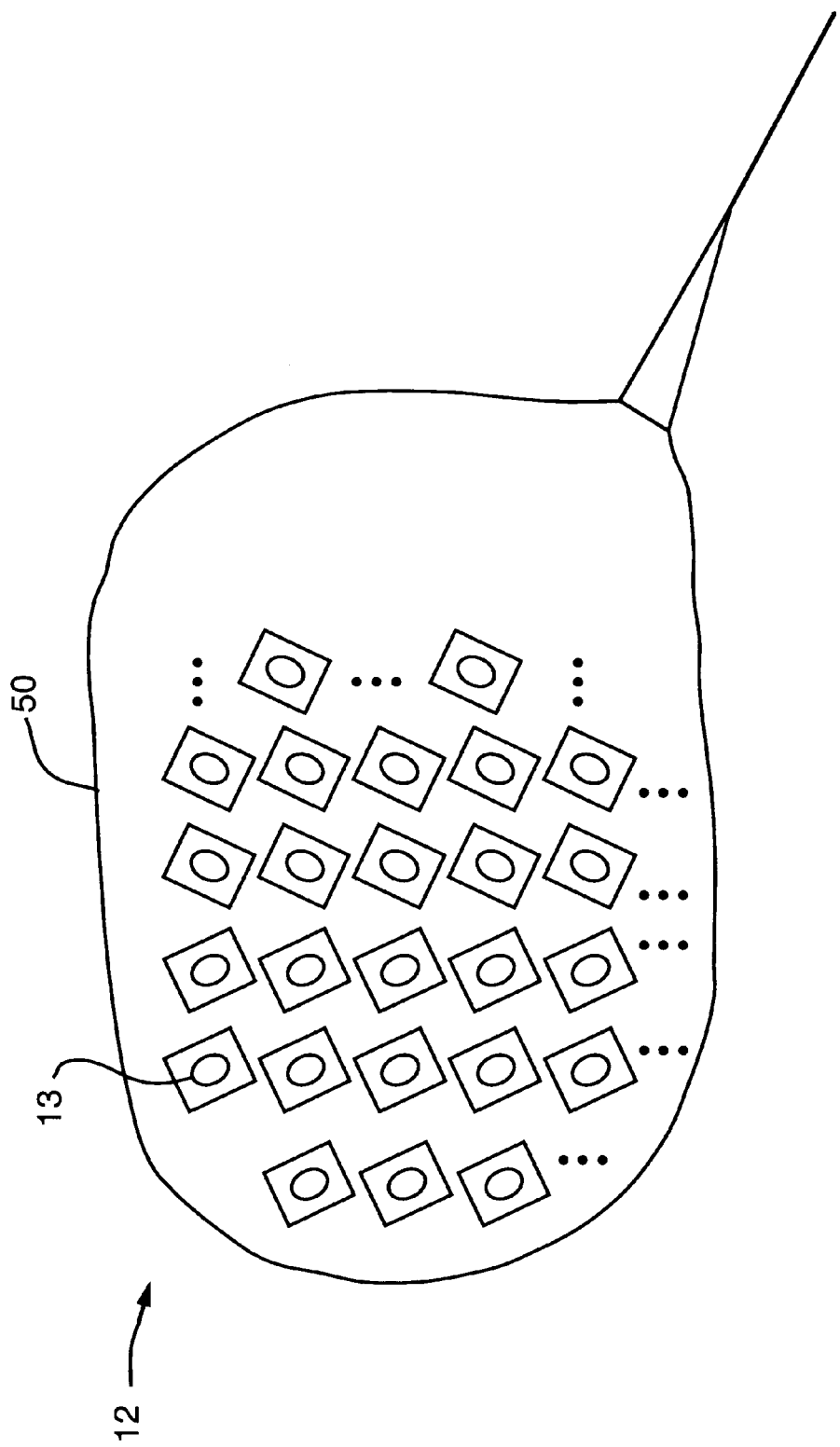
FIG. 5 depicts a transducer included in the system of FIG. 1.

Referring now to FIG. 5, the transducer 12 includes at least NP piezo-electric elements 13. The elements are grouped and spaced to produce at least N beams in each of the P planes, with N beams spanning the plane. As discussed above, the last of the P planes forms a 70° angle with the first of the P planes. A controller (not shown) operates the elements 13 in an appropriate order. Preferably, the elements are operated sequentially to produce in order all of the beams associated with the first plane, then the beams associated with a next plane, and so forth.

The piezo-electric elements 13 are dimensioned such that they produce divergent beams at their resonant frequency. Each element 13 thus produces a cone-shaped beam pattern for the transmission of the ultrasonic beams and the reception of the echoes. Consequently, each element is capable of responding to acoustic energy traveling along any ray that lies within the associated cone-shaped region. It is thus tolerant of angular displacement that lies within a range defined by the angle that the cone-shaped beam pattern subtends at the element. In order to strike an optimal balance between tolerance to angular orientation and the level of "noise" introduced into the signal, the dimensions of the element are selected such that the associated cone-shaped beam profiles subtend an angle, at the element, that is in an approximate range of 5° to 15°.

The piezo-electric elements 13 are mounted in a relatively thin pad and/or substrate 50. The elements are completely encased in an elastomeric material such that the surfaces that come in contact with the patient's skin are soft and conform to the contours of the abdominal region. Further, the elastomeric material is chosen so that it provides acoustic impedance matching with the skin, in order to minimize acoustic reverberations at the skin/transducer interface. There is thus no need for ultrasound gel, or a gel substitute, as is typically required with known prior devices.

Additionally, the elastomeric material is chosen such that the beams produced by the elements refract in a predetermined manner away from the normal at the transducer/skin interface. Accordingly, the actual physical tilt of the elements necessary to direct the acoustic beams towards the bladder are significantly smaller than with known prior devices. This allows the transducer 12 to be significantly thinner in profile than the known prior transducers, and the transducer 12 can thus be worn more conveniently and comfortably by a user.

Figure 6:
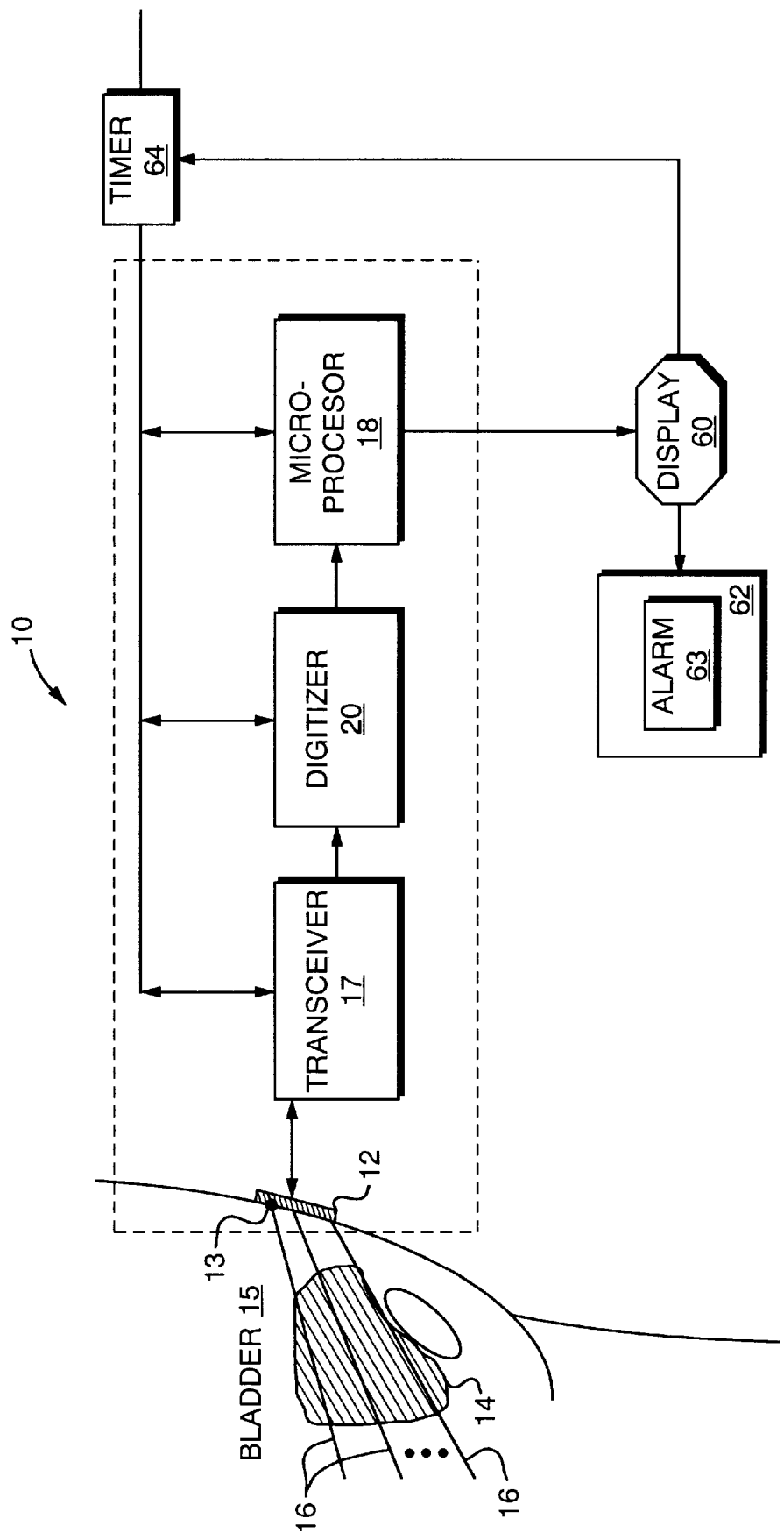
FIG. 6 is a functional block diagram of the system of FIG. 1 with optional components.

Referring now to FIG. 6, the system 10 may include a display device 60 that displays and/or stores the volume estimate. The system may also, or instead, include an alarm sub-system 62 that compares the volume estimate with a predetermined minimum voiding threshold, and sets off an alarm 63 if the estimate meets or exceeds the threshold. The alarm, which notifies the user of the need to void, may be a visible, audible or vibrational alarm, as desired. The system preferably repeats its monitoring operations at predetermined time intervals, under the control of a timer 64. Once the estimated volume exceeds 75% of the pre-established minimum threshold value, the system increases the frequency with which the monitoring operation is performed. The system may also retain the estimates, to provide a patient history.

The foregoing description has been limited to a specific embodiment of this invention. It will be apparent, however, that variations and modifications may be made to the invention, with the attainment of some or all of its advantages. For example, the system may be used to estimate the volume of fluid in any fluid-filled organ that is surrounded by soft tissue. Further, the various processors and sub-processors may be hardware, software or firmware. Therefore, it is the object of the appended claims to cover all such variations and modifications as come within the true spirit and scope of the invention.

What is claimed is:

1. A system for estimating the volume of fluid in an organ, the system including:
   A. a transducer for
      i. providing to a region of a body in which the organ is situated a plurality of ultrasonic beams that section the organ into a plurality of transverse planes that are angularly offset from a first transverse plane and section each transverse plane into a plurality of subsections;

ii. receiving from the region echoes that correspond to the beams, and iii. producing A-line signals that are associated with the echoes;

B. means for determining in each of the plurality of A-lines associated with a given plane locations of front and back walls of the organ;

C. means for determining an outline of the organ in the given plane based on the locations of the front and back walls in the plurality of A-lines associated with the plane;

D. means for calculating a cross-sectional area of the organ in the given plane based on the outline of organ in the plane; and E. means for determining an estimate of the volume of fluid as the weighted sum of the cross-sectional areas calculated for the planes, with the weight assigned to a given area being associated with the angle the corresponding plane makes with an approximately horizontal plane.

2. The system of claim 1 wherein the transducer produces at least NP beams, where P is the number of planes and N is a number of beams that span a given plane.

3. The system of claim 1 wherein the transducer produces beams that span planes that form an angle of approximately 70° between a last plane and the approximately horizontal plane.

4. The system of claim 1 wherein the means for determining locations of front and back walls in the A-line signals includes one or more filters for filtering noise from the signal and enhancing edges in the signal.

5. The system of claim 1 wherein the means for determining an outline of the organ fits a first curve to the front wall locations associated with the given plane and a second curve to the back wall locations associated with the plane.

6. The system of claim 5 wherein the means for calculating an area of the organ uses Simpson's Rule to determine in the given plane the area under the second curve that is associated with the back wall locations and the area under the first curve that is associated with the front wall locations, and subtracts the two areas to calculate the cross-sectional area of the organ in the plane.

7. The system of claim 1 wherein the transducer remains in a given position and sequentially produces the plurality of ultrasonic beams associated with a given plane, followed by the plurality of ultrasonic beams associated with a next plane, and the plurality of ultrasonic beams associated with each successive plane until the beams associated with all of the planes are produced.

8. The system of claim 1 wherein the transducer includes:

a. a plurality of piezo-electric elements that are arranged to produce ultrasonic beams that section the bladder into the plurality of planes and each plane into a plurality of subsections;

b. a relatively thin pad that houses the piezo-electric elements, the pad being acoustically impedance matched to skin; and c. means for controlling the operation of the piezo-electric elements, to operate them sequentially to produce the ultrasonic beams that span and section each of the plurality of planes without repositioning the transducer or moving any of the piezo-electric elements.

9. The system of claim 8 wherein each piezo-electric element is dimensioned to produce a divergent beam when the element is operated at a resonant frequency.

10. The system of claim 1 further including a timer that controls the times at which the system produces the estimates.

11. The system of claim 10 wherein the timer decreases the time between estimate calculations if the previous estimate is within a predetermined percentage of an overflow threshold.

12. The system of claim 1 further including an alarm that is energized if the volume estimate exceeds a predetermined overflow threshold.

13. The system of claim 1 ftirther including means for storing the volume estimates.

14. A system for estimating the volume of fluid in an organ, the system including:

A. a transducer that remains in a given position on the body, the transducer providing to a region in which the organ is situated a plurality of ultrasonic beams that section the organ into a first transverse plane and a plurality of transverse planes that are angularly offset from the first plane and section each transverse plane into a plurality of subsections, and producing corresponding A-line signals, the transducer including:

a. a plurality of piezo-electric elements that are arranged to produce ultrasonic beams that section the bladder into the transverse planes and each plane into a plurality of subsections;

b. a relatively thin pad that houses the piezo-electric elements, the pad being acoustically impedance matched to skin;

c. means for controlling the operation of the piezo-electric elements, to operate them sequentially to produce the ultrasonic beams associated with each of the respective planes;

B. means for determining locations of front and back walls of the organ in the plurality of A-lines associated with a given plane; and C. means for calculating a volume estimate based on the locations of the front and back walls of the organ in each of the transverse planes.

15. The system of claim 14 wherein the means for calculating the volume includes:

i. means for determining an outline of the organ in the given plane based on the locations of the front and back walls in the plurality of A-lines associated with the plane;

ii. means for calculating a cross-sectional area of the organ in the given plane based on the outline of organ in the plane; and iii. means for determining an estimate of the volume of fluid as the weighted sum of the areas calculated for the planes, with the weight assigned to a given area being associated with the angle the corresponding plane makes with an approximately horizontal plane.

16. The system of claim 14 wherein the transducer produces at least NP beams, where P is the number of planes and N is a number of beams that span a given plane.

17. The system of claim 14 wherein the transducer produces beams that span planes that form an angle of approximately 70° between a last plane and the approximately horizontal plane.

18. The system of claim 14 wherein each piezo-electric element is dimensioned to produce a divergent beam when the element is operated at a resonant frequency.

19. The system of claim 14 further including a timer that controls the times at which the system produces the estimates.

20. The system of claim 19 wherein the timer decreases the time between estimate calculations if the previous estimate is within a predetermined percentage of an overflow threshold.

21. The system of claim 14 further including an alarm that is energized if the volume estimate exceeds a predetermined overflow threshold.

22. The system of claim 14 further including means for storing the volume estimates.

* * * * *